United States Patent [19]

Landwehr

[11] Patent Number: 4,639,107
[45] Date of Patent: Jan. 27, 1987

[54] ACQUIRING MEASUREMENTS OF AN OBJECT BY MEANS OF PHOTOGRAPHY

[76] Inventor: Ulrich M. Landwehr, Bahnhofstr. 8, 1 OG, D-300 Hannover 1, Fed. Rep. of Germany

[21] Appl. No.: 750,862

[22] Filed: Jul. 1, 1985

[30] Foreign Application Priority Data

Jul. 13, 1984 [DE] Fed. Rep. of Germany ....... 3425913

[51] Int. Cl.⁴ .............................................. G03B 29/00
[52] U.S. Cl. ................................................... 354/77
[58] Field of Search ..................... 354/75, 76, 77, 110, 354/290

[56] References Cited

U.S. PATENT DOCUMENTS

| | | | |
|---|---|---|---|
| 1,482,068 | 1/1924 | Douglass | 354/110 |
| 1,482,070 | 1/1924 | Douglass | 354/110 |
| 1,596,458 | 8/1926 | Schiesari | 354/77 |
| 3,495,518 | 2/1970 | Takagi et al. | 354/75 |
| 4,370,039 | 1/1983 | Landwehr | 354/77 |

Primary Examiner—Michael L. Gellner
Attorney, Agent, or Firm—Ralf H. Siegemund

[57] ABSTRACT

The dimensions of an object are acquired photographically under utilization of a measuring raster, to be imaged in addition to a projected horizontal line raster, either by placing a raster containing plate next to the imaging plane of the camera, or by projecting a measuring raster into the camera laterally, under utilization of a semi-transparent mirror.

8 Claims, 4 Drawing Figures

ACQUIRING MEASUREMENTS OF AN OBJECT BY MEANS OF PHOTOGRAPHY

BACKGROUND OF THE INVENTION

The present invention relates to the acquisition of dimensions of an object under utilization of photography, the object being particularly the contour of a human body.

Methods of the type to which the invention pertains, use for example photography, i.e. photographic images of an object are to be produced together with a superimposed measuring raster, whereby simultaneously a particular raster is projected during imaging in an oblique direction and from above, being comprised primarily of horizontally running lines. Such an apparatus and reference is for example disclosed in my U.S. Pat. No. 4,370,039. This method uses particularly a vertically split imaging system, wherein during one step, one half of a single exposure film strip area is exposed so the object itself and in one particular position, while a measuring raster is imaged onto the other half or the film strip area. Subsequently, object and raster exchange position, whereby the object, i.e. for example a person assumes a different position or posture and his or her image is photographically superimposed (double exposure) upon the previously photographed raster while the same measuring raster as an object is in a similar kind of double exposure position, superimposed upon the object of the first taken picture.

This procedure and apparatus was found to be very advantageous, particularly as compared with previously known techniques for measurement, and it was found particularly that measurements of the object could be taken in this manner in a very accurate fashion. Particularly for orthopedic procedures, this method can be used with advantage because health-damaging X-rays can be avoided. The particular method permits particularly the acquisition of information concerning posture, physical damage, illnesses of the human skeleton, such as scoliosis, or hip bone distortions, uneven leg length or the like. The technique as described permits the acquisition of objective data, so that for example subsequently the success of therapy can be objectively evaluated.

The aforementioned equipment and method however, has the drawback that the superpositioning of the two photographs require a change in position of the person. From an objective point of view, and particularly from a method and equipment point of view, this is no disadvantage. It was found however, that in some cases frail humans cannot simply be asked to undertake this change in position.

It is therefore an object of the present invention to simplify the known method and to avoid the application drawbacks outlined above.

DESCRIPTION OF THE INVENTION

In accordance with the preferred embodiment of the present invention, the object is achieved, in that the measuring raster is projected directly into the image plane of the camera during taking of a picture of the object. Thus contrary to the known technique there are no double exposures necessary, i.e. it is not necessary to superimpose two pictures on one film strip area in a sequential procedure, but a single image taking is sufficient, provided there is a measuring raster projected into the image plane, which is adequate and suitable for measuring the individual. It is essential in this case of course, that the measuring raster is properly adjusted.

In order to carry out the inventive concept it was found advantageous for instance to prepare a slide of the measuring raster to be arranged immediately in front of the imaging plane for directly projecting that slide onto the film in a contact-printlike fashion.

The slide is preferably made of a transparent material such as glass, into which metal fibers of a diameter of a few tenths of a millimeter have been embedded. Alternatively lines could have been printed on, etched on, painted on, or the like, onto a transparent carrier. Also a metallic grid arranged directly in front of the image plane will fulfill the desired purpose. In this case of course the raster lines will appear as black lines on the developed film.

Alternatively for practicing the invention, it may be of advantage to project a measuring raster into the imaging plane under utilization of the objective lenses projecting medium. The measuring raster will be arranged to the side, and projection is provided through a semi-transparent mirror being arranged between the raster defining "object" and the objective lens of the photographic camera. The mirror permits the taking of the picture of an object, simply because the mirror is at least to some extent transparent to light, while the measuring raster is simultaneously projected into the imaging plane. It should be pointed out, that the term projected can be understood in two ways: directly by way of imaging using the objective lens above or through a composite process of slide projection as will be explained. Any resulting loss in light, on account of the mirror of course can be compensated simply through longer exposure or brighter illumination. It was found that that does not present any problem.

Equipment for carrying out the inventive principle may include a camera as well as a flash light projector arranged above the camera and providing a horizontal line pattern as per my earlier suggestion. In accordance with a specific teaching of the present invention, a slide is for example arranged inside the camera, in between objective lens and imaging plane which slide as stated includes a measuring raster, the distance between slide and imaging plane should be less then 0.5 millimeter, preferably even below 0.2 millimeter, but parallelism to the imaging plane has to be observed. In order to make sure that the lines of the measuring rasters are sharply imaged in the image plane one should simply provide the distance between measuring raster and imaging plane as small as possible. The measuring raster, i.e. the slide having nearly the same size as the image in the plane as stated, are made of extremely thin lines, metal wires, fibers, or the like. By way of example for an ordinary 35 mm imaging process one may use up to 60 horizontal and up to 50 vertical raster lines in the slide.

In a different configuration for practicing the invention a light transparent mirror is interposed between object and objective lens at an angle of preferably 45 degrees to the imaging plane. A measuring raster carrying plate is arranged directly, as a photographic object perpendicularly to the imaging plane and at a certain distance between the semi-transparent mirror. It is important in this regard that this raster carrying plate has as far as the relevant geometry is concerned, the same or the equivalent distance to the objective lens as the object itself, because the plate is concurrently photographed with the true object e.g. a person.

In lieu of the plate one may use a slide projector which projects a slide into the imaging plane of the camera. The slide in this case carries the measuring raster and of course the objective lens of the camera augments and supplements the objective lens of the projector.

It is a significant advantage of the present invention, that one does not need anymore a double exposure type of procedure. Since the measuring raster is projected directly into the imaging plane it is not necessary to move the object, only the posture for example of a person can be changed in order to take a second shot from a different angle. But the person himself has no longer, so to speak, move across the stage. It was found that this simple improvement in practicing the invention, is quite instrumental in an environment in which the object, so to speak, is a handicapped person.

DESCRIPTION OF THE DRAWINGS

While the specification concludes with claims, particularly pointing out and distinctly claiming the subject matter which is regarded as the invention, it is believed, that the invention, the objects and features of the invention, and further objects, features and advantages thereof will be better understood from the following description taken in connection with the accompanying drawings, in which:

Proceeding now to the detailed description of the drawings, reference is made presently to FIGS. 1 and 2. FIG. 1 illustrates a side view of an inventive picture taking arrangement, wherein reference numeral 1 refers to a camera, being for example of the instant kind. A flashlight projector 2 is arranged above the camera 1 and directs a line raster image as a flash of spatially modulated light into an object plane 3. The projector 2 projects a line raster during the taking of an image of object 3, onto the person this is described for example in greater detail in my U.S. patent.

A person is presumed to stand for example on a so-called balancing scale which provides for example an indication of an uneven posture. A balancing scale of this kind is for example described in German printed patent application No. 310,186 4 which however does not pertain to the present invention, and is mentioned here only for purposes of completion. A scale of this kind is moreover illustrated for example in the file for U.S. trademark registration No. 1,317,710.

Figure 1:
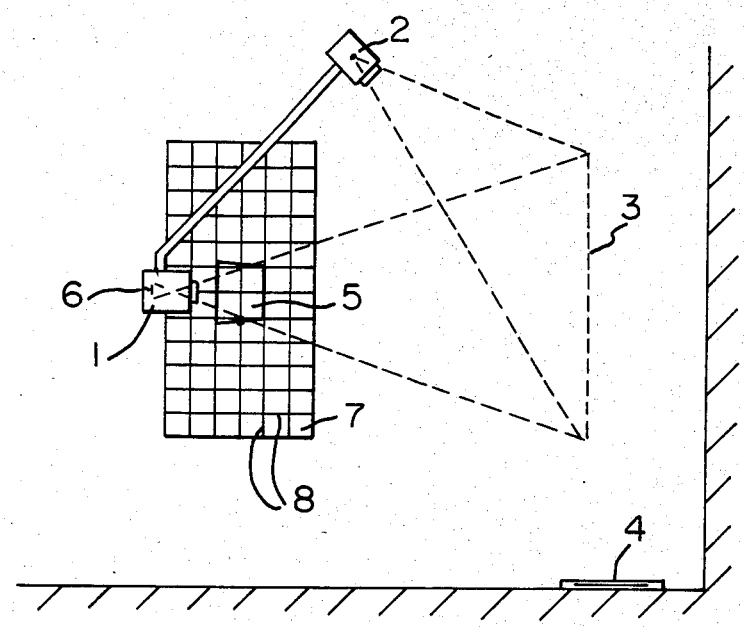
FIG. 1 illustrates a cross section and side elevation through an arrangement for practicing a preferred embodiment of the present invention.
Figure 2:
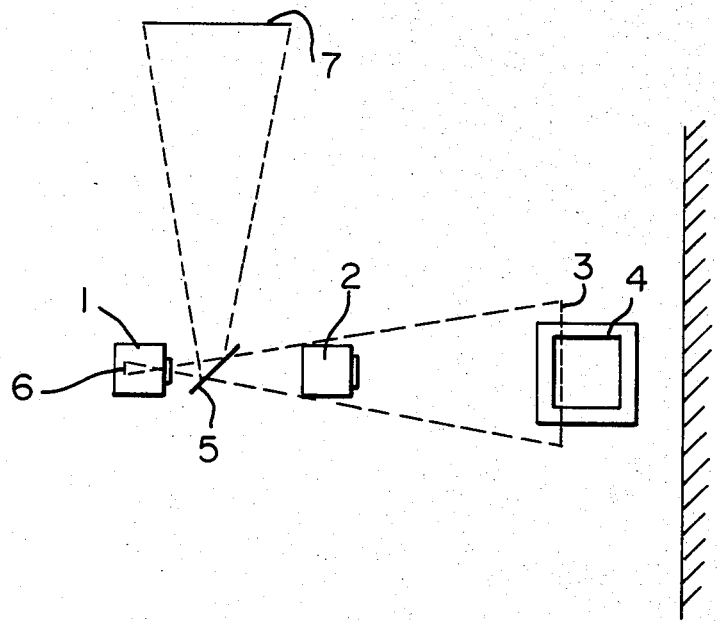
FIG. 2 is a top elevation of the equipment shown in FIG. 1.

Directly in front of camera 1 is provided a semitransparent mirror 5 arranged as can be seen best from FIG. 2 at an angle of 45 degrees to the plane 3 of the object as well as to the imaging plane 6 inside camera 1. A raster 8 is provided as, so to speak, secondary object being visible in plan view in FIG. 1 and being composed of raster lines 8 provided in same contrasting fashion on a background plate 7. The distance of that plate 7 from say the semitransparent mirror 5 is the same object 3 has from that mirror. Thus the object plane 3 as well as the raster plate 7 are now imaged by the camera upon the film in image plane 6 in superimposing relationship as provided by the mirror 5.

Figure 3:
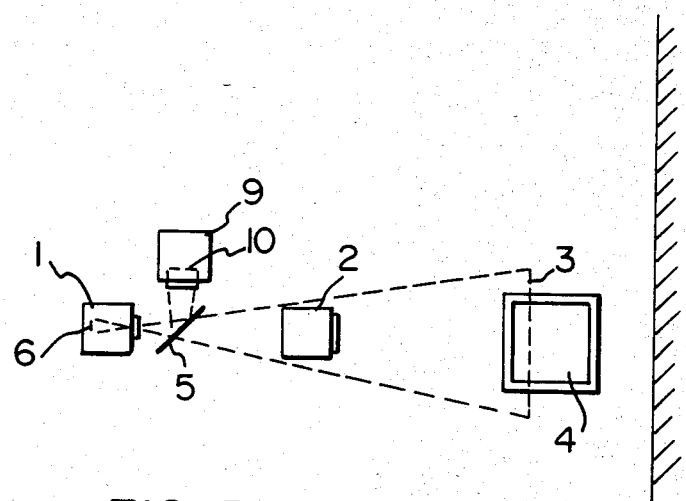
FIG. 3 illustrates an alternative embodiment for practicing the preferred embodiment of the present invention.

FIG. 3 illustrates a different arrangement. Again camera, a balancing scale, an object plane and a semitransparent mirror 5 are the same as shown in FIGS. 1 and 2. However a slide projector 9 is provided for projecting a slide 10 onto the mirror 5 to be reflected into the camera. The slide 10 of course carries a measuring raster of optically contrasting vertical and horizontal lines. The projection as such will be carried out simultaneously (overlappingly in the temporal sense) with the taking of the picture. Since the mirror 5 is semitransparent, there is indeed again a superpositioning of images.

Common to the examples shown thus far is that either the measuring raster on the plate 7, or the slide 10 may have a dark or a bright background and bright or dark raster lines. The slide 10 may be a blackened plate with etched in or cut in raster lines or the slide 10 is clear and raster lines are painted on, printed on or fibers bonded into the glass, having the configurations of extremely thin wires, as was mentioned in the introduction.

Figure 4:
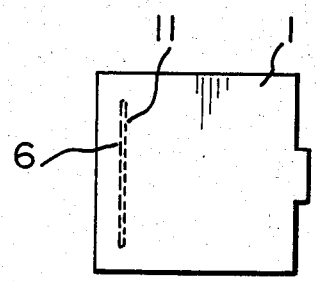
FIG. 4 is a schematic view of the interior of the camera for practicing the most simple embodiment of the present invention, being preferred for that reason.

Still another and preferred embodiment of the invention is shown in FIG. 4. Basically the arrangement is as shown in FIGS. 1 and 2, except the semi-transparent mirror 5 is omitted, so that accordingly there is no raster plate 7 or slide projector 9 provided. Instead the camera is modified in that immediately in front of the film and imaging plane 6, a slide 11 has been inserted, made of a transparent material and carrying for example extremely thin filaments, wires or the like delineating the raster pattern. In fact then on taking a picture a contact print of that slide 11 is made also onto the film in imaging plane 6. It is clear that the spacing between the imaging plane 11 and particularly the wires on the slide 11 should be very small in order to avoid fuzzy imaging. A few tenth of a millimeter at the most should be permitted here.

The invention is not limited to the embodiments described above, but all changes and modifications thereof, not constituting departures from the spirit and scope of the invention are intended to be included.

What is claimed is:

1. In an imaging method for ascertaining the dimensions of an object by means of photography, including the step of projecting during imaging in an oblique direction a particular pattern of horizontal lines upon the object to be imaged, the improvement comprising:
projecting during photographic imaging a measuring raster of horizontal and vertical lines directly upon and into the imaging plane in a photographic camera.

2. Method as in claim 1, including the step of placing a slide with a measuring raster directly next to the imaging plane in the camera.

3. Method as in claim 1, and including projecting under utilization of a semi transparent mirror and through an objective lens of the camera, a measuring raster directly into the imaging plane of the camera.

4. Method as in claim 3, wherein said projection step includes, providing a measuring raster in form of a secondary object and at a distance from the camera equivalent to the distance between object and camera, for superimposing the measuring raster as an image through operation of the semi-transparent mirror using the objective lens of the camera for purposes of projection.

5. Method as in claim 3, and including the step of using a slide projector, there being a raster carrying slide that is being projected by means of the slide projector into the camera.

6. Apparatus for acquiring the dimension of an object including a photographic camera, the improvement comprising:
   a flash projector, disposed for projecting a flash image of a horizontal line raster upon said object and at an oblique angle;
   a semi-transparent mirror placed at an angle in front of the camera; and
   means for superimposing a two-dimensional measuring raster upon the image through lateral projection upon an image produced by the camera or the object.

7. Apparatus as in claim 6, wherein said means for projecting includes a raster plate having an optical distance from the camera which is the same as the object has from a camera imaging plane.

8. Apparatus as in claim 6, including a slide projector for projecting a slide, carrying a measuring raster through the semi-transparent mirror upon the imaging plane in the camera.

* * * * *